United States Patent [19]

Brown et al.

[11] Patent Number: 5,382,268
[45] Date of Patent: Jan. 17, 1995

[54] METHOD AND APPARATUS FOR USE IN MICROPROPAGATION

[75] Inventors: Frank R. Brown, Clifton; William P. Billington, Flitwick, both of England

[73] Assignee: British Technology Group Ltd., London, England

[21] Appl. No.: 842,098
[22] PCT Filed: Sep. 19, 1990
[86] PCT No.: PCT/GB90/01447
§ 371 Date: Mar. 2, 1992
§ 102(e) Date: Mar. 2, 1992
[87] PCT Pub. No.: WO91/3929
PCT Pub. Date: Apr. 4, 1991

[30] Foreign Application Priority Data

Sep. 21, 1989 [GB] United Kingdom ............ 8921403

[51] Int. Cl.⁶ .................................. A01G 9/00
[52] U.S. Cl. .................................... 47/1.01
[58] Field of Search ..................... 47/1.01, 1 A

[56] References Cited

U.S. PATENT DOCUMENTS

| | | | |
|---|---|---|---|
| 3,514,900 | 6/1970 | McDade | 47/58 |
| 4,469,931 | 9/1984 | Macken | 219/121 LG |
| 4,569,914 | 2/1986 | Molnar et al. | 47/58 |
| 4,748,980 | 6/1988 | Cremer et al. | 128/303.1 |
| 4,782,728 | 11/1988 | Thatcher . | |

FOREIGN PATENT DOCUMENTS

| | | |
|---|---|---|
| 2377241 | 8/1978 | France . |
| 262787 | 12/1988 | Germany . |
| 2043517 | 10/1980 | United Kingdom . |
| 2202723 | 10/1988 | United Kingdom . |
| 1073914A | 6/1985 | U.S.S.R. ............ 47/58 |

OTHER PUBLICATIONS

A. F. Balabak et al., Sep. 1988, "The Effect of γ and Laser Radiation on the Rate of Rooting of Stem Cuttings of Coniferous and Evergreen Deciduous Plants".
J. M. Bonga and D. J. Durzan, May 1985, "Tissue Culture in Forestry".

Primary Examiner—Ramon S. Britts
Assistant Examiner—Joanne C. Downs
Attorney, Agent, or Firm—Cushman, Darby & Cushman

[57] ABSTRACT

In a method of cutting plant tissue for micropropagation, a container (42) containing plantlets (43) Is rotated on a turntable (19). A laser beam (35) is focused on a side wall (36) of the container below the level of a nutrient medium (45). The container (42) is rotated while the laser (35) cuts free an upper portion (36) of the container (12). After cutting, plant material is cut in a subsequent step by the same laser. Preferably the container is inverted during cutting of container and plantlets.

15 Claims, 11 Drawing Sheets

METHOD AND APPARATUS FOR USE IN MICROPROPAGATION

The present invention relates to a method and apparatus for use in micropropagation.

Micropropagation of plants uses the techniques of plant tissue culture and applies them to the propagation of plants. Micropropagation normally uses either shoots or shoot tips or other vegetable plant organs as starting points. At its simplest, micropropagation consists initially of excising small pieces of actively growing tissue. Then, under sterile conditions, the pieces of tissue are transferred to a nutrient medium which supports plant growth. The plant material will finally develop into entire plantlets. These plantlets must then be weaned from the axenic conditions in which they have existed within the laboratory into viable, rooted plants capable of survival in conventional horticultural or agricultural environments.

The growth of plants from tissue culture is a technique which can produce large numbers of genetically identical plants, perhaps possessing a desirable quality such as disease resistance, in a short time. The tasks of dissecting and transplanting such plants are labour-intensive and repetitive, and the gains in speed, sterility and labour costs which could be achieved by the use of robots make automation an attractive prospect for the fast-expanding micropropagation industry.

The present technique is labour-intensive, and two of the particularly important operations which are repeated frequently are removing a plant from a container, and cutting a required portion of plant tissue from the donor plant. As performed at present, commercially, the cutting operation normally consists of an operator removing plantlets from a plastics container, and cutting the plant material by a scalpel while holding the plant material with forceps. The standard container for plantlets is usually similar to a margarine tub, and, before the cutting operation can take place, the lid of the container is removed manually.

Two particular problems arise in the automation of micropropagation techniques. Firstly, there is the problem, in common with manual operation, of contamination of the plant material. This can arise either from contamination of the initial batch of multiplying cultures or by contamination during multiplication. In present commercial practice rule of thumb is that tools which contact plant material in one growing box are sterilized before use with the next box of plants. In the commonly used 80 mm diameter margarine tub there may be as few as four cultures yielding a total of twelve sub-cultures for transfer to fresh media. This example would be extreme, but serves to illustrate the importance of securing sterilization routines which can be effected with minimum interruption to output.

One particular source of contamination, is the process of removing the lids of the container. Another source is contact by the plants with the outer sides of the containers.

Another problem is that in robotic work on micropropation, there is often an awkward movement resulted by end effectors, e.g. anthropomorphic gripping devices, in entering into an open container, and manoeuvring inside the container whilst avoiding contact with side walls.

It is one object of the present invention to allow automatic or semi-automatic robotic manipulation of plant material during micropropagation whilst overcoming or reducing problems concerned with sterilization and manoeuvrability within plant containers.

According to the present invention in one aspect there is provided a method of operating on plantlets during micropropagation including the steps of presenting at a work station a container containing plantlets growing in a nutrient medium, and cutting the container by a laser to provide access to the plantlets.

Preferably the method includes using the laser to cut a normally upper portion of the container free from a normally lower portion which contains the nutrient medium supporting the plantlets, and removing the said upper portion of the container to provide access to the plantlets. Conveniently the step of removing the upper portion of the container after cutting may comprise removing the upper portion by forced gas flow, usually forced air flow, which may be achieved by blowing air or by suction.

The method may include cutting an opening in the top of a container but normally the method will comprise cutting a side wall or side walls of a container by the laser.

The method is particularly applicable when the plantlets are growing in the nutrient medium in a closed sterilised container. Preferably the cutting is effected by cutting the container by laser at a level within the depth of the nutrient medium in the container.

The method of the invention is particularly applicable in an automatic or semi-automatic system of micropropagation, which includes the step of manipulating the container and/or plant material by robotic handling means, for example under the control of a video camera for producing image signals of the work station.

Preferably the step of cutting the container includes focusing the beam of the laser to a cutting focus at a side wall of the container, and rotating the container during the cutting of the container. The method may include the step of adjusting the position of the cutting focus of the laser during the rotation of a non-circular container, in such a manner as to maintain the laser beam focused at the side wall of the container during cutting.

The method may include using the laser also to cut a portion of plant tissue from one of said plantlets. The step of cutting the plant tissue by the laser may comprise cutting the plant tissue from a plantlet while the plantlet is supported in the nutrient medium, or may comprise cutting the plant tissue after the plantlet has been removed from the container.

Thus, it is an advantage of the present invention, that where a laser is provided for cutting the plantlets, the laser may also be used for the further purpose of removing an upper portion of the plant container. Thus particularly economical use is made of the single laser to effect two unrelated operations.

The use of the laser for cutting the container gives a number of other advantages, at least in preferred embodiments. The laser cuts the container without introducing any contamination to the wall of the container, since no direct contact is made by a blade. Similarly, there Is no contamination of a blade by the container wall, and no requirement for sterilizing such a blade after the cutting operation. Thus, advantages include firstly provision of easy access to the plantlets after removal of the upper portion of the container, and secondly the removal of a major source of contamination, that is to say by the external surfaces of the upper part of the container.

The invention has particular advantage where the side wall of the container is cut at, or below the level of the nutrient medium, since this then leaves the plants standing entirely free of any surrounding side wall. This allows easy access to the plants by a robotic end effector, without danger of touching side walls of the container.

Although it is preferred that the invention includes the step of cutting the container by laser, and cutting the plant material by laser, other arrangements are possible. For example the method may combine laser cutting of the container with mechanical cutting of plant tissue, or laser cutting of container with both laser cutting and mechanical cutting of tissue. For example it may be appropriate, with some species, to restrict the use of the laser to severing the stem of the plant, thereby leaving the unwanted basal portions in the container, and then to dissect the plant by mechanical means.

There will now be set out a preferred aspect of the invention relating to the orientation of the container. Preferably the method of the invention includes the step of presenting at the work station a container having a normally lower portion containing the nutrient medium and a normally upper portion extending in the upward direction in which the plants normally grow, and presenting the container at the work station in an orientation different from the normal orientation, with the normally upper portion of the container at a lower position that usual relative to the normally lower position. Preferably the container is at least partly inverted, most preferably completely inverted with the plantlets extending downwardly from the nutrient medium. Preferably the cut away upper portion is removed at least partly by gravity. Preferably the said container is cut in such a manner that, when cut, the normally upper portion falls apart free from the normally lower portion.

In accordance with another preferred feature, the method includes the step of cutting by a laser through a plurality of the growing plantlets presented in an orientation different from the normal orientation, with normally upper portions of the plantlets at a lower position than usual relative to normally lower portions of the plantlets, to release in bulk cut away portions large enough to contain tips and/or nodes. Preferably the plantlets are presented for cutting with the container at least partly inverted. Most preferably the plantlets are presented for cutting with the container completely inverted and the plantlets extending downwardly from the nutrient medium. Preferably the cut away plant portions are removed from the remaining plantlets at least partly by gravity.

In accordance with another preferred feature the method includes cutting through the said plurality of growing plantlets at a substantially predetermined distance from the nutrient medium to release a first plurality of plant portions containing tips and/or nodes, and repeating the cutting step at a further, smaller, predetermined distance from the nutrient medium, to produce from the remaining cut stems before regrowth a further plurality of cut plant portions. Preferably the method includes carrying out the cutting step at a series of different distances from the nutrient medium to produce a series of pluralities of cut plant portions. Preferably the released plant portions are received onto a second nutrient medium positioned below the plantlet in the first container. Conveniently the method may include depositing the cut plant portions at random on the surface of a fresh nutrient medium.

In general those aspects of the invention which have been described with reference to a method according to invention, may also be provided with reference to apparatus according to the invention, and vice versa.

In particular, there may be provided in accordance with the invention in one aspect apparatus for use in micropropagation comprising means for presenting at a work station a container containing plantlets growing in a nutrient medium, and means for operating a laser to cut the container to provide access to the plantlets.

Conveniently, the operating means includes means for rotating the container during cutting, and also preferably means for focusing the beam of the laser on a side wall of the container, and for adjusting the position of the focus of the laser during rotation of a non-circular container, so as to maintain the focus of the laser located at the side wall of the container. Conveniently the adjusting means comprises cam means corresponding to the shape of the container, and a cam follower for adjusting the position of the focus of the beam of the laser.

In some preferred arrangements the said means for presenting the container at the work station is adapted to present a container having a normally lower portion containing the nutrient medium and a normally upper portion extending in the upward direction in which the plants normally grow, the presenting means being adapted to present the container at the work station in an orientation different from the normal orientation, with the normally upper portion of the container at a lower position than usual relative to the normally lower position. The apparatus may include means for operating a laser to cut through a plurality of growing plantlets in the container presented in an orientation different from the normal orientation, with normally upper portions of the plantlets at a lower position than usual relative to normally lower portions of plantlets to release cut away plant portions large enough to contain tips and/or nodes, and second support means for supporting a second nutrient medium, the second support means being arranged in a position such as to receive in bulk the released plant portions cut by the cutting means.

In accordance with the invention in another aspect there is provided a method of cutting plant tissue for micropropagation comprising the steps of cutting plant tissue by use of a laser, and utilising the laser in at least one additional operating step other than cutting the plant material.

Embodiments of the invention will now be described by way of example with reference to the accompanying drawings in which:

FIG. 8 is a front view of the device of FIGS. 7a and 7b, shown when in the closed position of FIG. 7a;

There will first be described, with reference to FIGS. 1 to 4, an embodiment of the invention for operating plantlets during micropropagation, in which a cylindrical container of plantlets is prepared for further processing steps during micropropagation. There will then be described a modification of the embodiment for use with containers of a non-circular cross-section.

Figure 1:
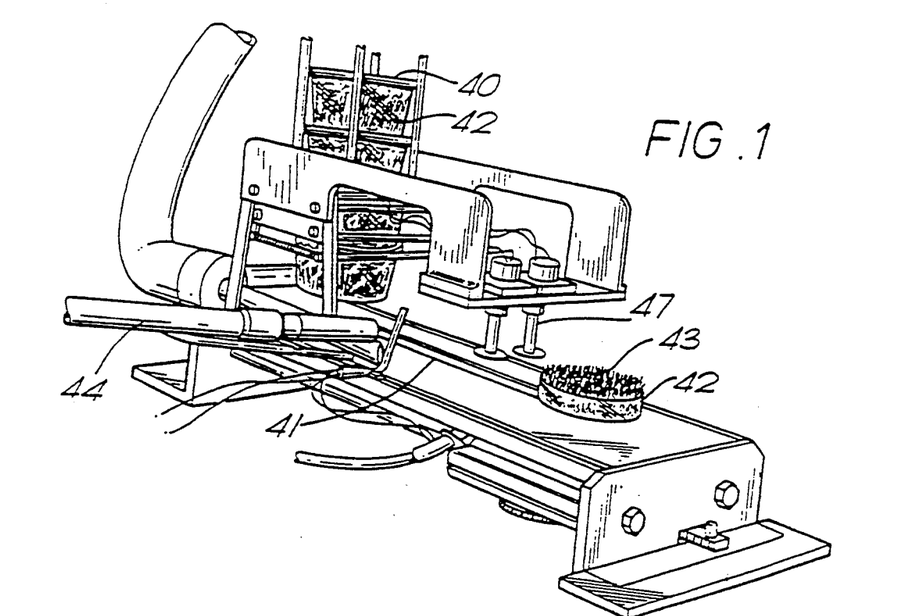
FIG. 1 is a perspective view of the general layout of apparatus embodying the invention for operating on plantlets in a container during a method of micropropagation.
Figure 2:
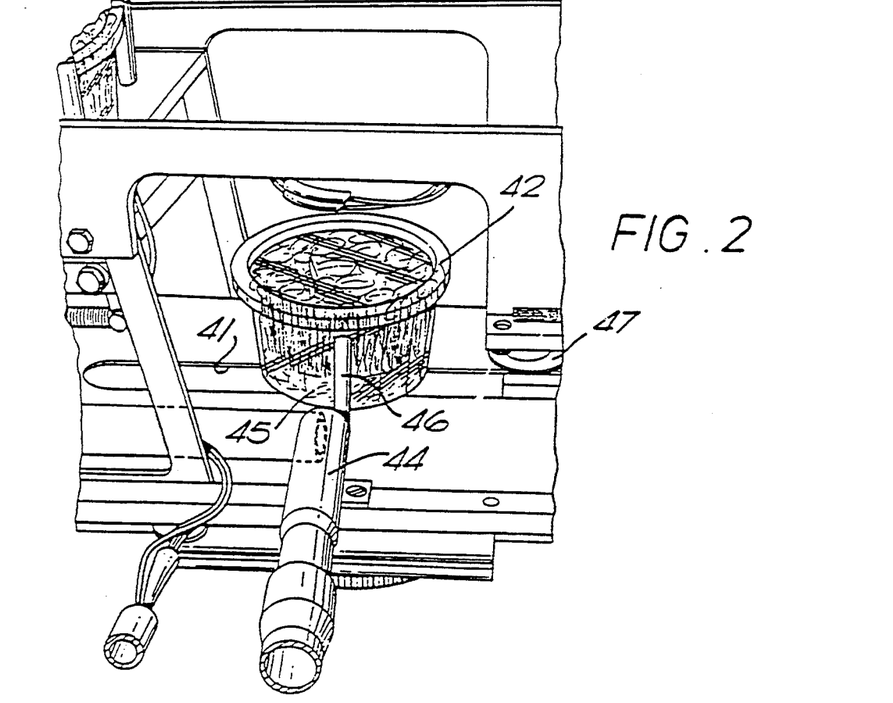
FIG. 2 shows part of the apparatus of FIG. 1 relating to the removal of an upper portion of a container for plantlets.
Figure 3:
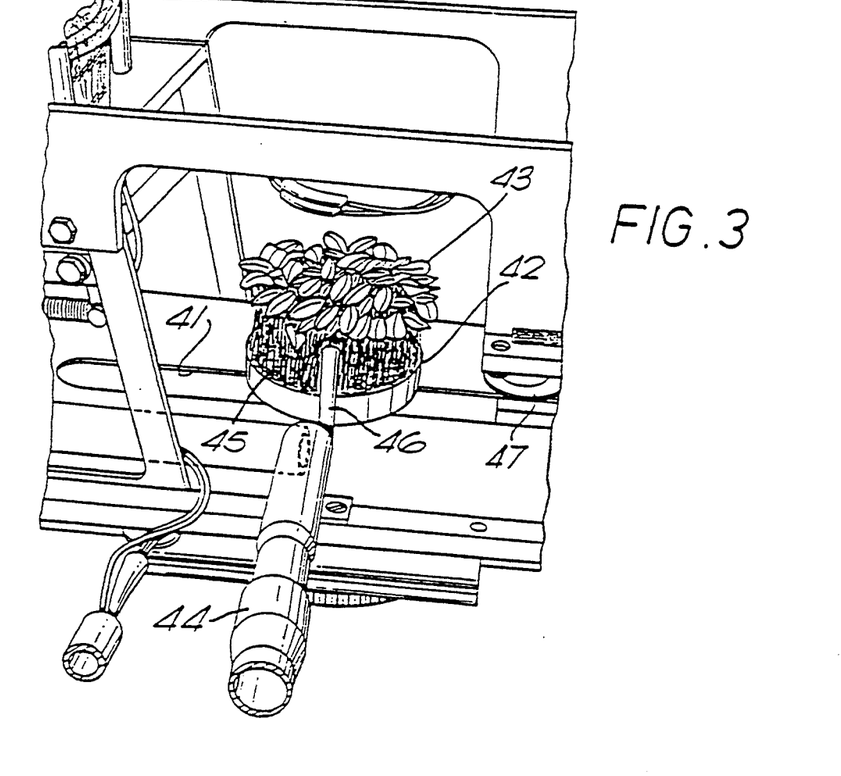
FIG. 3 is a side perspective view of the same apparatus part as shown in FIG. 2, but after the removal of the upper portion of the container.
Figure 4:
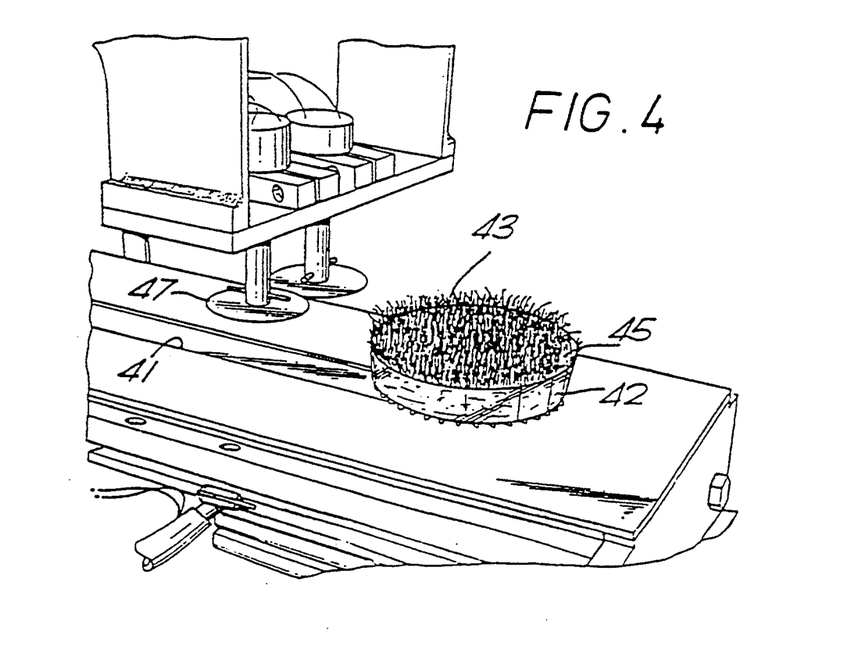
FIG. 4 shows a further portion of the apparatus of FIG. 1, and illustrates plant material after removal of the upper parts of the foliage of the plants.

The main parts of the first embodiment are shown in FIG. 1, and consist of a stacking assembly 40 positioned over a conveyor belt 41, for handling containers 42 of plantlets 43 during micropropagation. The containers 42 are stacked in the stacker 40 and dispensed one at a time onto the conveyor 41. The conveyor carries a suction pad (not shown) onto which a container 42 is placed, so that the container is held firmly in place on the conveyor. Thus firstly a container 42 of plantlets is deposited from the stacker 40 onto the conveyor and is conveyed to the right in FIG. 1. At a first work station in FIG. 2, the container 42 is halted beside a laser 44. The container 42 is then rotated on the suction pad while the laser 44 is focussed to cut through the container 42 at a level just below the level of the agar or other nutrient medium 45 in the container 42. After cutting, the upper portion of the container 42 is removed by a blast of compressed air along a nozzle 46. This leaves easy access to the plantlets 43, as shown in FIG. 3. Next, the container 42 and plantlet 43 are moved to the right beneath a pair of high speed contra-rotating serrated disc cutters 47, to remove unwanted foliage from the plantlets. The cut foliage is removed by a further blast of compressed air, along a further nozzle (not shown). This leaves the base portions of the plantlets 43 ready for selection and division, as shown in FIG. 4.

By way of example, the next step in a micropropagation method may be that the opened container 42 shown in FIG. 1 may be observed from above by a video camera (not shown) in a vision guidance system, which is linked to a robotic end effector (also not shown). The end effector is positioned over the container 42 and is then lowered so as to grip a plantlet to be divided, by gripping elements of the end effector. The end effector is then operated through a sequence in which a plantlet is held and cut, under the control of the vision guidance system. Conveniently the plantlet may be cut by a laser beam taken from the same laser that has been used to cut the container. The laser beam for cutting the plantlet may be directed by a further focussing device coupled to the same laser. Alternatively, the plantlet may be cut by a mechanical blade, or other means. The cut plantlet is then lifted by the end effector and moved to a work station where a further container of fresh nutrient medium has been positioned to receive cut plant portions.

An alternative to cutting an upper portion of the container away in the way described, is to cut the container by two separate cuts. Firstly a cut may be made vertically up one side of the container, across the top of the container, and then down the other side to the level of the nutrient medium. After this a further cut can be made around the side of the container as has been described already. The consequence of such a cutting arrangement is that two halves of the lid fall apart free at the end of the cut, and can more easily be blown or otherwise removed from the cutting station.

It is to be appreciated that throughout the embodiment described, the principles of the invention may apply equally to a situation where the actual lid has been removed from the container before cutting away the sides of the container. Thus the container being cut may be an already open container, rather than a completely closed container.

Various modifications of the embodiment shown in FIGS. 1 to 4 will now be described with reference to FIGS. 5 to 7. Components which correspond to components described previously, will be indicated by like reference numerals.

Figure 5:
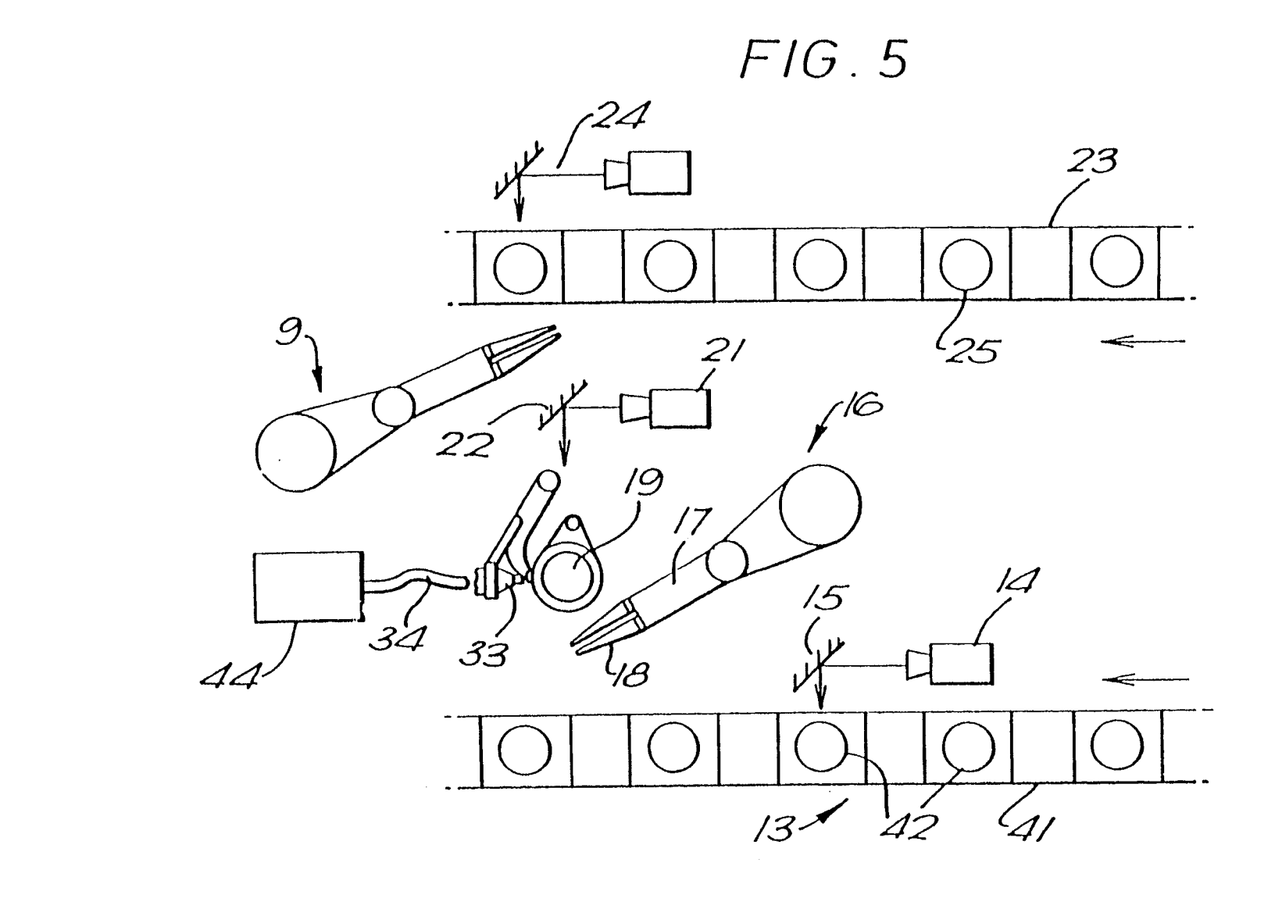
FIG. 5 is a diagrammatic representation of the general layout of apparatus for cutting plant tissue for micropropagation, embodying the invention.

FIG. 5 shows a diagrammatic plan view of a robotic system for use in micropropagation of plants. A conveyor belt 41 carries a series of containers 42 containing plantlets growing during micropropagation. The conveyor 41 is operated intermittently and a container 42 is arrested at a work station 13 beneath the line of vision of a video camera 14 directed at a mirror 15. A microprocessor (not shown) is linked to the output of the camera 14, and also to a robotic end effector 16 comprising a robot arm 17, and manipulating fingers 18.

A turntable 19 is provided to receive the containers 42, and a laser 44 is positioned adjacent the turntable 19, the laser 44 and turntable 19 being observed by a further camera 21 and mirror 22, all these elements also being under the control of the microprocessor. Finally, a further conveyor 23 and further camera 24, are provided to remove plant material which has been operated on.

It is to be appreciated that the conveyor 41, robotic arm 16 turntable 19, and other elements shown in FIG. 5 are not drawn to the same scale.

In this particular modification, the end effector 16 picks up a container 42 from the conveyor belt 41 and transfers it to the turntable 19. Part of the container is then cut away in accordance with the invention, as will be described hereinafter, and the cut portion of container is removed by the end effector 16 or by air blast. A further end effector 9 (which has not contacted the containers 42) then cooperates with the laser 44, to effect desired cutting operations on the plantlets from the container, and required portions of plant material are transferred to fresh growing material in containers 25 on the conveyor belt 23.

Figure 6:
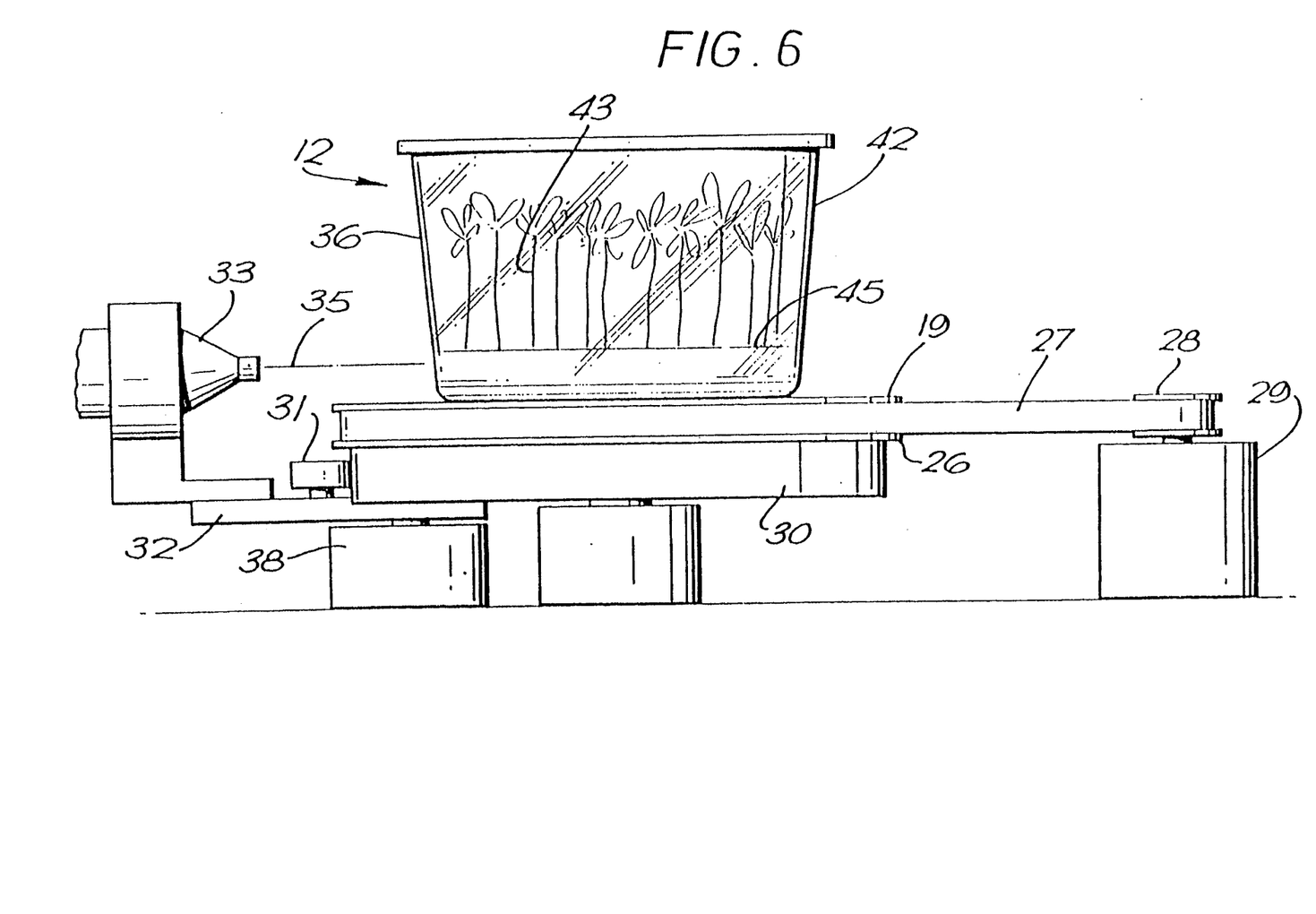
FIG. 6 is a diagrammatic side view of apparatus for cutting a container of plantlets and embodies the present invention.
Figure 7:
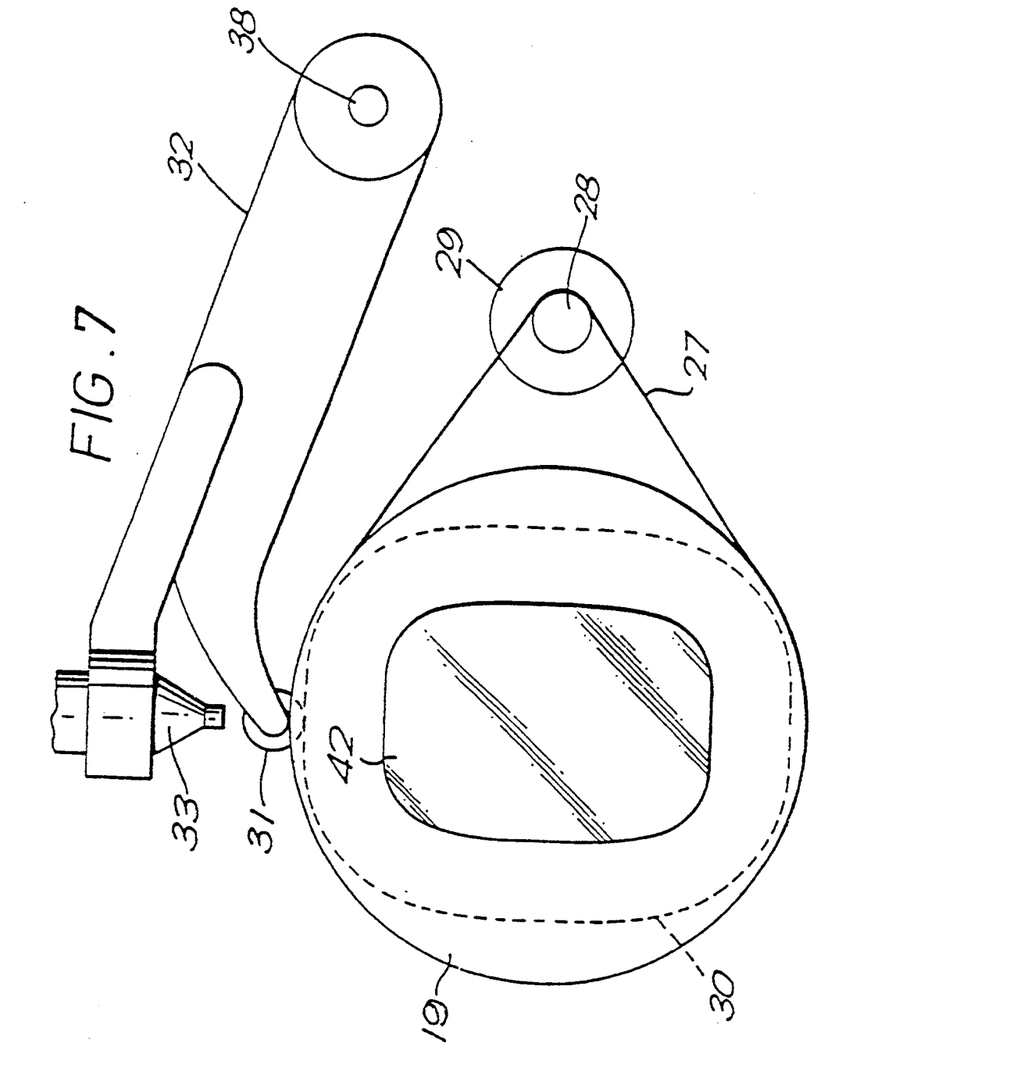
FIG. 7 is a diagrammatic plan view of the apparatus of FIG. 6.

Turning now to FIGS. 6 and 7, there will be described in detail how the upper part of a container 42 is removed in accordance with the invention. Referring to FIG. 6, the turntable 19 has an upper surface on which rests the container 42. Preferably a recess for the container is provided, but this has been omitted for simplicity. The turntable 19 forms a drive pully 26 cooperating with a drive belt 27 which is driven by a further drive pulley 28 mounted on a drive motor 29. Below the drive pulley 26 is a cam 30 which has approximately the same shape as the outline of the container 42 (as shown in FIG. 7). The output beam of the laser 44 emerges at a moveable end lens 33 connected to the laser 44 by a flexible optic fibre coupling 34. A cam follower 31 is mounted on a laser support arm 32 which is pivoted about a pivot bearing 38, and is biased (by means not shown) towards the cam 30 For the best effect the cam profile is shaped to be slightly differently from the outline of the container, to compensate for the obliquity of the laser beam due to the rotational movement of the arm 32 carrying the laser lens.

In operation the laser beam, indicated diagrammatically at 35, is focused on a side wall 36 of the container 42, preferably at a level slightly below the level of nutrient medium 45 (e.g. agar) in the container 42. The turntable 19 is then rotated at a speed appropriate to the power of the laser, and during rotation the laser end lens 33 is moved towards and away from the turntable 19 under the control of the cam follower 31, so as to maintain the focus of the laser beam at the side wall of the container.

After the cutting of the upper portion 12 of the container, the free upper portion 12 is removed by the end effector 16, or by a pulse of air flow, leaving the plantlets easily accessible to a further end effector 9. Other steps can then conveniently be carried out, for example the further end effector 9 may grasp and remove plantlets from the nutrient medium 45, transfer the plantlet to the focus of the laser 44, and allow cutting of the plant material. Alternatively, the plantlet may be held by the end effector 9 and severed by the laser 44, leaving the end effector 9 free to transfer the cut plantlet to a further, sterilised, work station (not shown), or to a container 25 on the conveyor 23. In addition to the cutting of the container the output of the laser may be directed by a further optical coupling means (not shown) to an entirely different work station, where further cutting operations take place. It is preferred that the actual steps of cutting required nodes from the plant material are carried out outside the container at a separate work station.

It is preferred that the laser beam is directed to cut the container at a level below (e.g. 2 mm below) the level of the agar 45 in the container. This allows the use of the agar to absorb any spare energy from the laser, so as to avoid damage to plantlets which might occur if the laser were directed at the side wall 36 but above the level of the agar 45. Another factor is that cutting of plastics material may release HCl or other toxic gas. If the cutting takes place below the level of the agar, the agar will to some extent seal the main interior of the container, and prevent or inhibit this gas entering into the environment of the plantlets during cutting.

The rate of rotation of the turntable 19 is set at a rate appropriate to the power of the laser, a faster rate of rotation being used at higher power levels. The time taken to cut round a typical container of the size of a margarine tub would be approximately 30 seconds.

In general, when the laser is used for cutting the plastics container, a beam of lower strength is used than for cutting the plant material in subsequent steps. By way of example, a suitable laser for use in cutting plant material is a 40 W $CO_2$ laser system. When used for cutting the container, the power used would only be about 4 watts.

In one example, means may be provided to split the laser beam to provide, from a single source, two beams of different total powers (e.g., 36 and 4 watts). This would allow lid removal and tissue cutting operations to take place simultaneously. The question then arises as to how to focus each of these beams to achieve optimum performance. With any focussing arrangement there is a trade-off between spot size and depth of focus. To cut thin wall plastics material it is preferable to use a sharply focussed beam which gives a small spot size (high energy intensity) and rapidly diverging beam (thereby reducing damage beyond the focal plane). For thicker materials such as plant tissue a greater depth of focus is desirable but this can only be achieved by employing a longer focal length lens system, which unfortunately results in a larger spot size. This accounts in part, for the requirement for more power to cut plant tissue.

The use of the cam 30 allows a simple means for adapting the turntable to containers of different shapes. Different cams may be provided for different shaped containers. As an alternative to a cam and cam follower, a proximity sensor may be provided which, contacts the side of the container, and which produces an output signal which is used to control the position of the focus of the laser beam. The proximity sensor may comprise a mechanical feeder, or an electrical fiducial sensor, which avoids physical contact with the container, so as to reduce the possibility of contamination.

To summarise, the advantages of the described embodiment of the invention are that cutting is carried out in conditions of sterility with reduced risk of contamination, and, after cutting, easy access is provided to the microplantlets for a robotic end effector.

As has been mentioned, in one aspect the invention is concerned with the use of a laser for cutting plant tissue, and the use of the same laser in an additional operating step other than cutting plant material. In the preferred embodiment described, the additional operating step is the cutting of the plant container by the laser. An alternative function which may be carried out by the laser is that the laser may be used for heat sealing a second container in which plantlets are planted. This requires using the laser at a lower energy intensity than for cutting, which can be arranged by defocusing the laser beam.

Referring to FIGS. 7a to 10, there is shown a device for use in embodiments of the invention described hereinbefore, for gripping and manipulating a plantlet during micropropagation procedures after removal of an upper part of a container containing the plantlets. The device 60, comprises a pair of cantilevered rollers 70 and 70A projecting from a pair of support members 65 and 65A which are pivotally mounted on a sub frame 61. The rollers are driven by respective stepper motors 73 and 73A and can be moved towards and away from each other by pivoting of the support members by means of a pneumatic cylinder. A plantlet can be gripped by controlled movement of the rollers apart and towards each other and can be lifted by rotation of the rollers in counter rotation.

Figure 9:
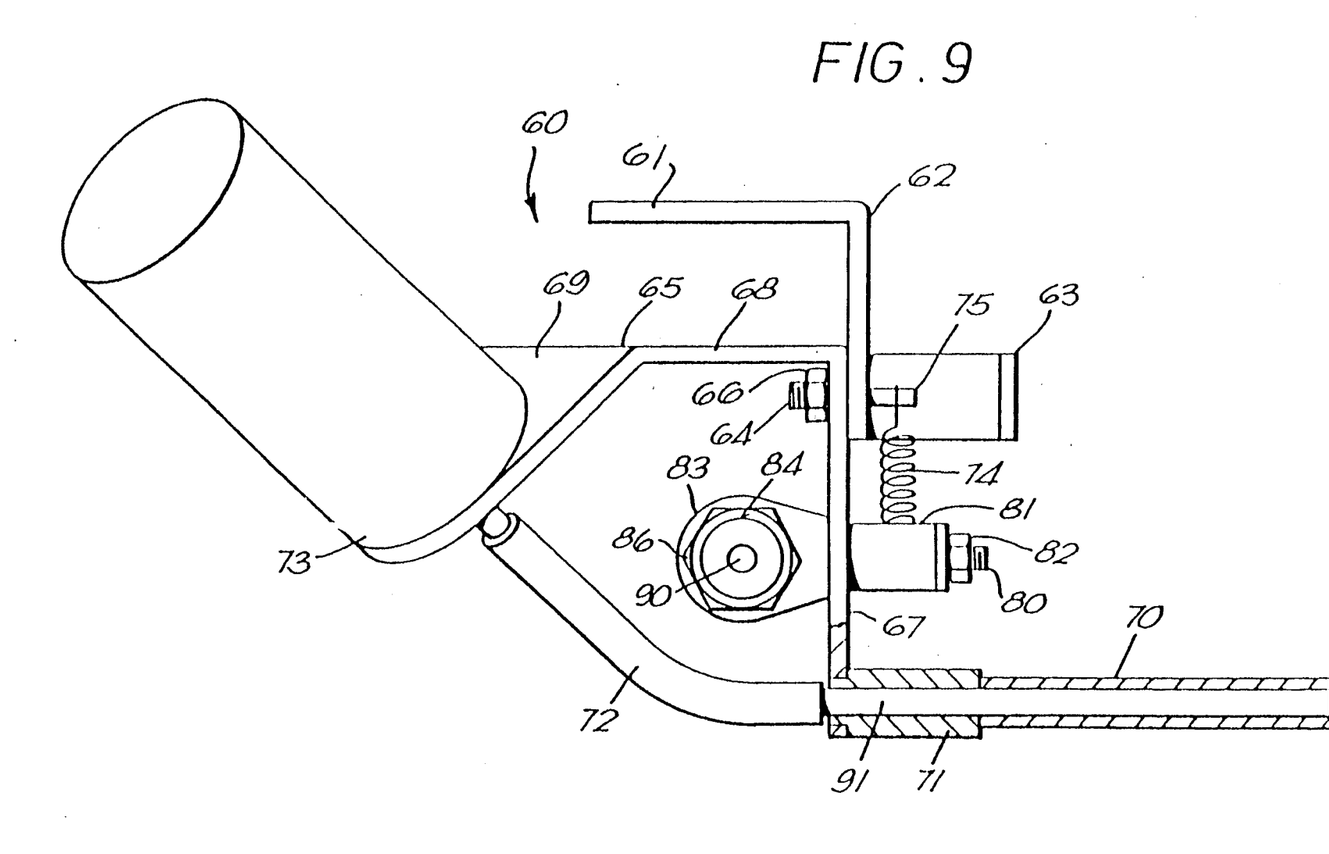
FIG. 9 is a side elevation of the device of FIGS. 7a and 7b, with a part section through one roller of the device.

Considering the device 60 in more detail, the sub-frame 61 has a main vertical flange 62 which carries two pivot assemblies 63 and 63A, each of which houses a pivot shaft 64 or 64A which protrudes rearwardly i.e. to the left in FIG. 9. The two main support members 65 and 65A are pivotally mounted on the vertical flange 62 of the sub frame 11, by means of the pivot shafts 64 and 64A. As shown in FIG. 9, the pivot shaft 64 extends through an aperture in the support member 65, to be secured by a nut. The pivot assembly 63 is arranged so that the support member 65 is freely pivotable about the axis of shaft 64. The second pivot assembly 63A has a similar shaft 64A on which is pivoted the second support member 65A.

As shown particularly in FIG. 9, the support member 65 comprises a main vertical flange 67, and a rearwardly extending horizontal flange 68 which leads to an end flange 69 Which is inclined at a skew angle to the horizonal flange 68. The horizontal flange 68 and vertical flange 67 of the support member 65 are strengthened by a gusset 69, which is omitted from the side view of FIG. 9a for simplicity. Protruding horizontally from the bottom of the vertical flange 67 is the rubber covered roller 70 which is rotatable about its longitudinal axis on a drive shaft 91 in a bearing 71 which is fixed relative to the flange 67. The roller 70 is coupled by a flexible drive, 72, for example a close coiled tension spring covered by a flexible plastics sleeve, to the geared electric stepper motor 73. The stepper motor 73 is mounted on the inclined end flange 69 of the support member 65, so that the entire sub-assembly of roller 70, motor 73, and support member 65, can pivot together about the pivot shaft 64.

Figure 7A:
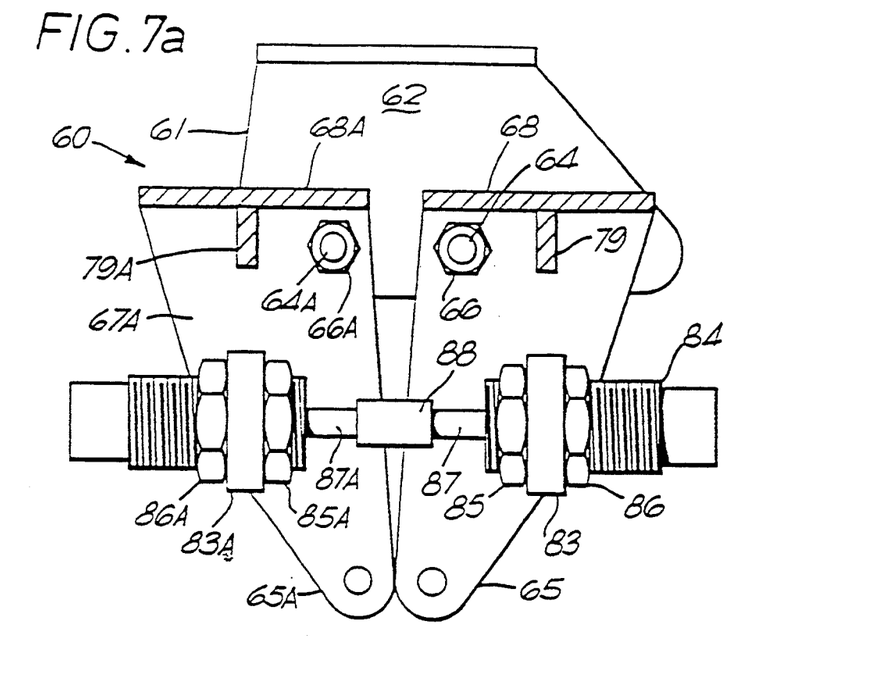
FIG. 7a is a rear view of a device for gripping and manipulating a plantlet, which may form part of an embodiment of the invention.
Figure 7B:
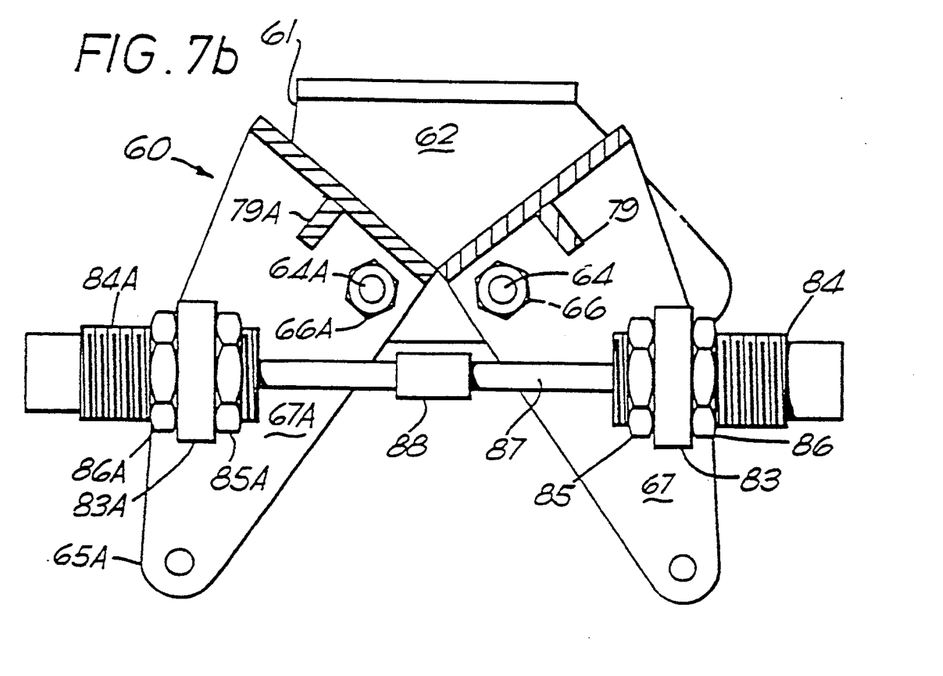
FIG. 7b is the same view as shown in FIG. 7a but with the device in an open position ready to pick up a plantlet.

Thus there has been described with reference to FIGS. 7a, 8 and 9, the left hand roller 70 in FIG. 8, and the components associated with that roller, all pivotally mounted by pivot shaft 64 on the sub-frame 61. Considering FIG. 8, it will be seen that the second roller 70A is supported in a similar manner on support member 65A which is pivoted about pivot shaft 64A on the sub-frame 61. Other components associated with the rotor 70A which correspond to the components associated with the rotor 70, are indicated by corresponding reference numerals followed by the reference letter A.

Certain features of the construction of the elements associated with the roller 70A are different from those associated with the roller 70. The support member 65A is coupled to the front flange 62 of the sub-frame 61 by a tension spring 74, which is linked between studs 75 and 76 on the sub-frame 61 and on the support member 65A, respectively. A further stud 77 acts as a stop which locates against a protruding finger 78 of the front flange 62 of the sub-frame 61. The effect of these components is to return the rollers 70 and 70A to a determinable datum position, relative to the sub-frame 61.

Figure 8:
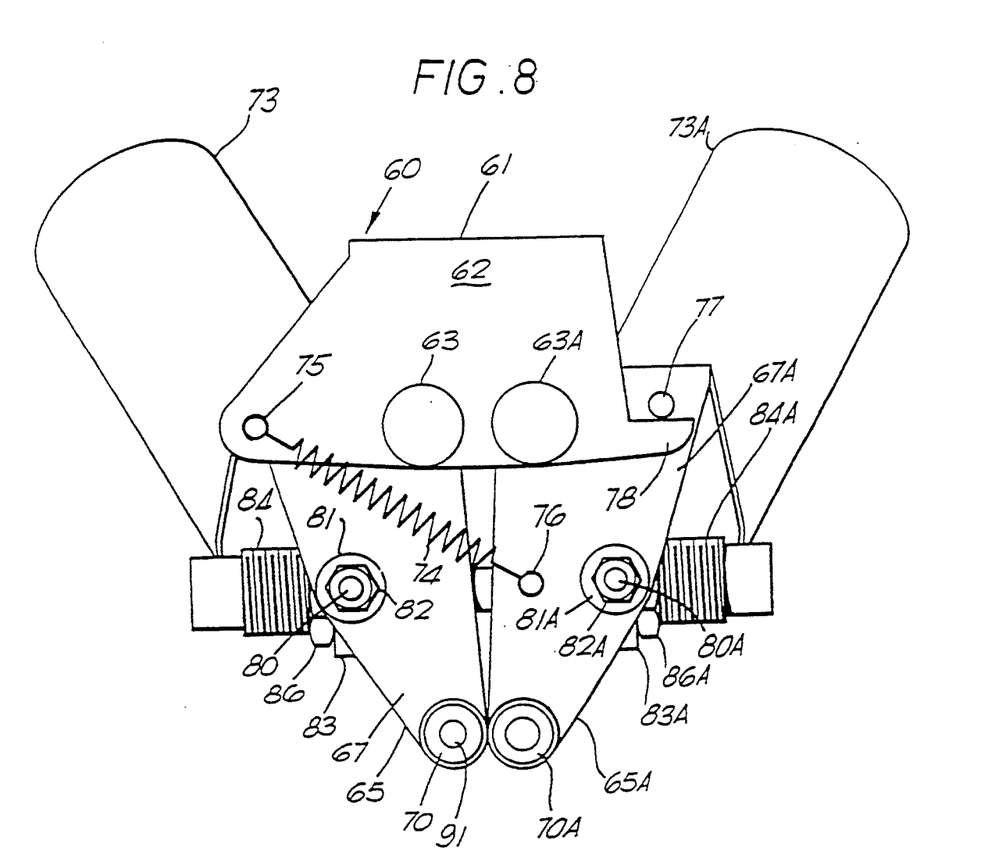

As shown in FIGS. 8 and 9, there is provided on support member 65 a further pivot shaft 80 which extends through the support member 65 into a pivot assembly 81, to be secured by a nut 82. The pivot shaft 80 passes through the support member 65 and forms a mounting plate 83 having a large central aperture (not visible). As shown in FIG. 7a, there extends through the aperture in the mounting plate 83 a pneumatic cylinder 84 which is threaded externally and is secured to the plate 83 by nuts 85 and 86. The piston rod 87 of the pneumatic cylinder 84 extends away from the plate 83 towards the centre line of the device, where it is coupled by a coupling 88 to a corresponding piston rod 87A associated with the other roller 80A. The corresponding mounting of a pneumatic cylinder 84A is indicated by corresponding reference numerals, followed by the reference letter A.

The two pneumatic cylinders 84 and 84A, constitute first drive means for moving the rollers 70 and 70A together and apart so as to grip items to be manipulated by the device. Air is fed to the pneumatic cylinders 84 and 84A through conduits 90 and 90A respectively, and when such air is supplied, the support members 65 and 65A are moved apart by pivoting about the pivot shafts 64 and 64A, to the position shown in FIG. 7b. When the air pressure is removed, the rollers 70 and 70A move back together again, and return to the datum position by operation of the spring 74 in FIG. 8. The pistons of the pneumatic cylinders are internally spring biased towards the retracted position and it is these springs which cause the support members 65 and 65A, and hence the rollers 70 and 70A, to move back together again when the air pressure is released. The spring 74 ensures the rollers return to the datum position.

The strength of the spring 74 is chosen to be sufficient to locate the rollers at the datum position, but not so great as to interfere with the operation of opening and closing the rollers. If the spring is so strong that the working pressure of the pneumatic cylinders cannot overcome its force then the roller 70A would not move at all. In fact this is not the case, as the retracting forces of the internal springs (not shown) in the pneumatic cyliners, together with the gravitational force on each roller assembly, ensure that when the system is at rest the rollers would reside more or less in the required datum position without any bias. It is therefore only necessary for a light spring 74 to provide a positive bias onto the datum stop 77.

Referring to FIG. 8, the sequence of events in use is as follows. When air pressure is applied to each cylinder, the roller 70 moves out on its pivot 63 until the boss of the pivot assembly 81 contacts the lower edge of the vertical flange 62. The roller 70A stays in the datum position during this phase, under the influence of the spring 74. At this point the roller 70 can move no further, and the roller 70A then pivots outwardly until the boss of the pivot assembly 81A also contacts the lower edge of the vertical flange 62. The whole assembly rests in this position whilst the air pressure is maintained. When the air pressure is released, the rollers return to the datum position in reverse sequence.

In addition to the rollers 70 and 70A being able to grip items by moving apart and together, items can also be gripped and manipulated by rotation of the rollers by the stepper motors 73 and 73A, which constitute second drive means for rotating the rollers in counter-rotation. Thus an item may be picked up either by the rollers 70 and 70A moving apart, and then back together again, and the rollers being moved upwardly, or by the item being positioned at the nip of the rollers, and being drawn upwardly by rotation of the rollers 70 and 70A. In some circumstances both actions may be used in order to pick up an item.

Figures 10, 11:
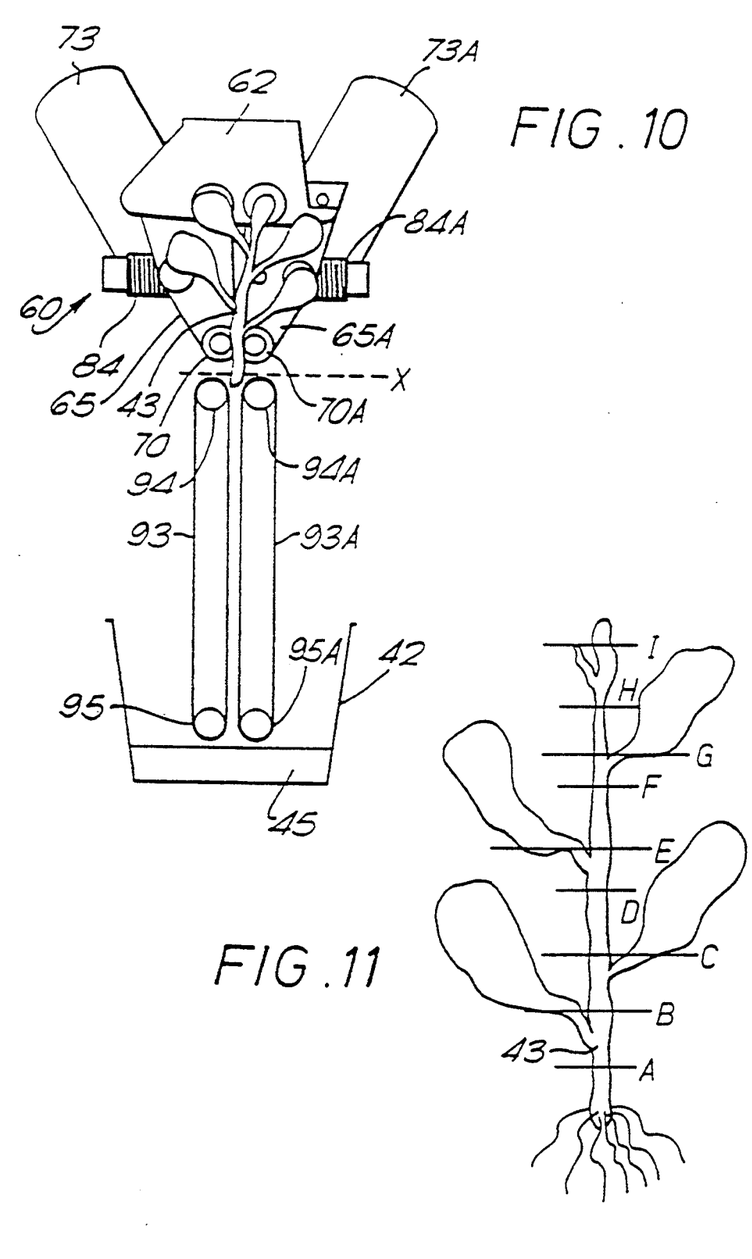
FIG. 10 is a simplified view corresponding to FIG. 8, but when used in operation together with other components of apparatus embodying the invention.
FIG. 11 is a diagrammatic representation of a plantlet, showing suitable lines of cut to obtain a series of nodes.

FIG. 10 shows the gripping device 60 of previous Figures, holding a plantlet 43 between the rollers 70 and 70A. Immediately below the rollers 70, 70A there are provided a pair of opposed conveyor belts 93 and 93A, running about rollers 94, 95, 94A and 95A, with parallel opposed faces of the conveyor belts 93 and 93A moving downwardly towards a nutrient medium 45 in a container 42. FIG. 10 shows a particular stage of use of the gripping device 60, but a description of a number of stages of use will be given referring to FIG. 10 as a convenient Figure where a plantlet 43 is held by the device 60.

FIG. 11 shows a plantlet 43 with a number of suitable cutting lines A to I for cutting the plantlet during micropropagation. The first step in the use of the gripping device 60 of FIGS. 7a to 10 is that the rollers 70 and 70A of the device 60 grip a plantlet 43 from a container 42 (such as that shown in FIG. 1), from which an upper portion of the container has been removed as previously described. The device 60 is then moved to a waste disposal work station (not shown) where a cut is made at A in FIG. 11 by a laser beam which is moved across the base of the plantlet by focussing means which will be described hereinafter with reference to the FIG. 12.

After removal of the root section, the plantlet 43 is moved to the position shown in FIG. 10, over the fresh nutrient medium 45. The rotors 70 and 70A are then rotated so as to feed the plantlet 43 downwardly into the pair of conveyors 93 and 93A. When sufficient of the plant has been fed downwardly to supply a node into the conveyor belts 93 and 93A, a laser cut is made across the line B in FIG. 11, which is arranged to lie horizontally between the upper pair of rollers 94 and 94A of the conveyor belts 93 and 93A, and the pair of roller grippers 70 and 70A. This line is indicated line is indicated at X in FIG. 10. The conveyor belts 93 and 93A then feed the cut node downwardly and insert it into the nutrient medium 45. This process is repeated by moving the nutrient medium horizontally relative to the lower rollers 95 and 95A, and then feeding a further node into the conveyors 93 and 93A, and cutting that node free along the line X in FIG. 10, corresponding to the line C in FIG. 11.

Figure 12:
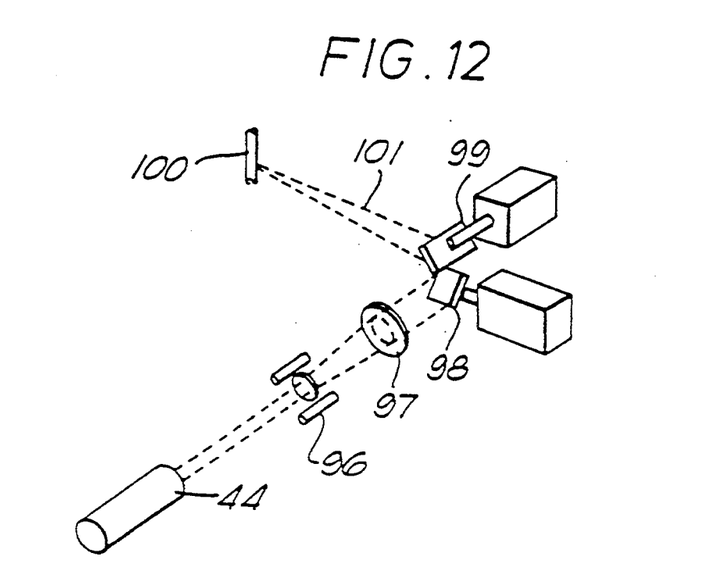
FIG. 12 is a diagrammatic representation of apparatus for focussing a laser for use in embodiments of the invention.

In FIG. 12, there is shown a diagrammatic representation of means for moving a laser beam, which may be used in accordance with a number of embodiments of the invention. As shown in FIG. 12, the laser 44 is focused by a moveable lens 96, and fixed focusing lens 97 to fall upon a pair of galvanometer mirrors 98 and 99. The beam 101 is finally focused at the stem of a plantlet represented diagrammatically by vertical line 100. The galvanometer mirrors are controlled electrically to sweep the laser beam 101 horizontally from side to side, when effecting a cut. The galvanometer mirrors 98 and 99 are linked automatically to the moveable lens 96 so that the laser beam 101 is always maintained in focus in a plane perpendicular to the beam. The arrangement of FIG. 12 may be used to effect the cuts shown in FIG. 11, as has been described also with reference to FIG. 10.

There will now be described with reference to FIGS. 13a and b and 14 an alternative embodiment of the present invention. The embodiment of FIGS. 13a and b and 14 is a modification of the embodiments described hereinbefore, and features of the various embodiments may be interchanged and utilised as appropriate. Where corresponding components appear in the various embodiments, they are indicated by like reference numerals.

Figure 13A:
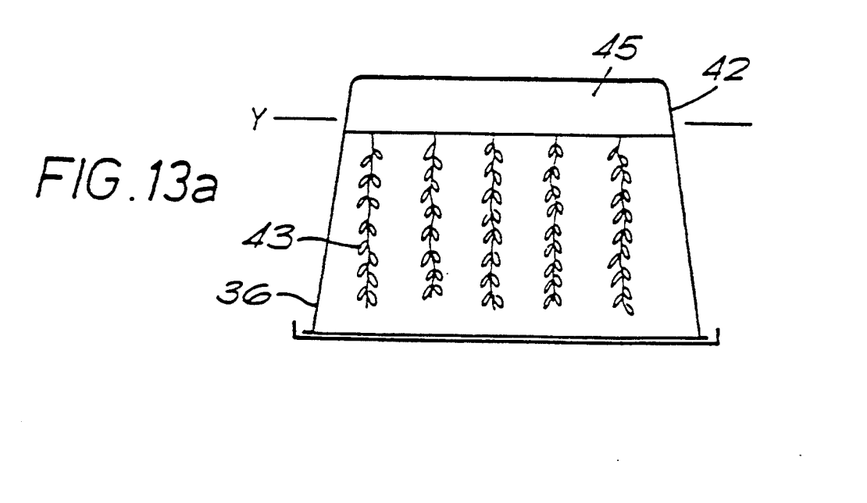
FIGS. 13a and 13b are diagrammatic representations of a container of plantlets during cutting operations in an embodiment of the invention.
Figure 13B:
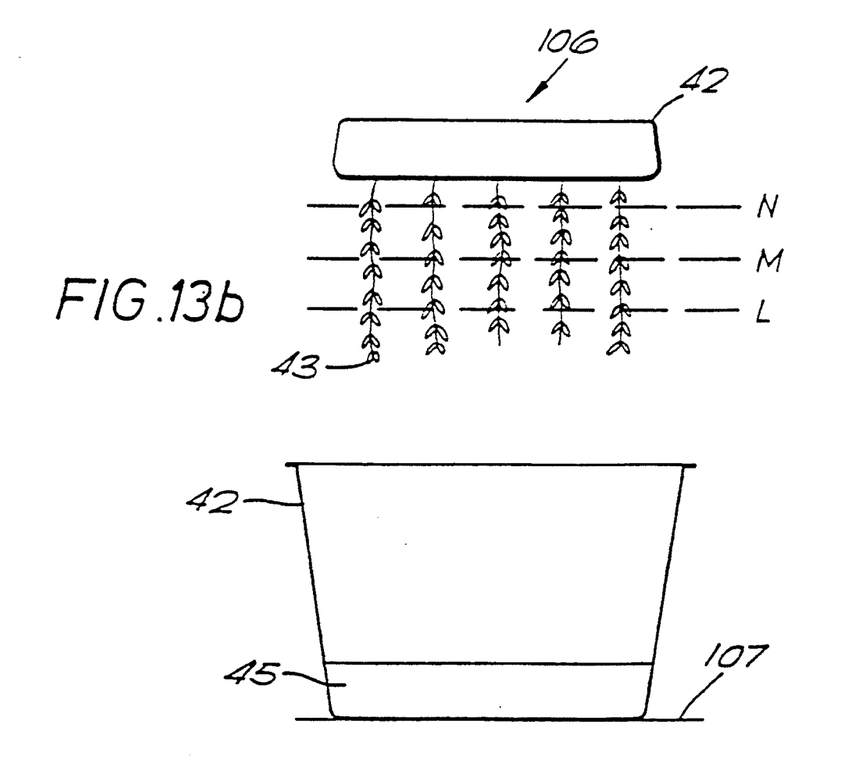
Figure 14:
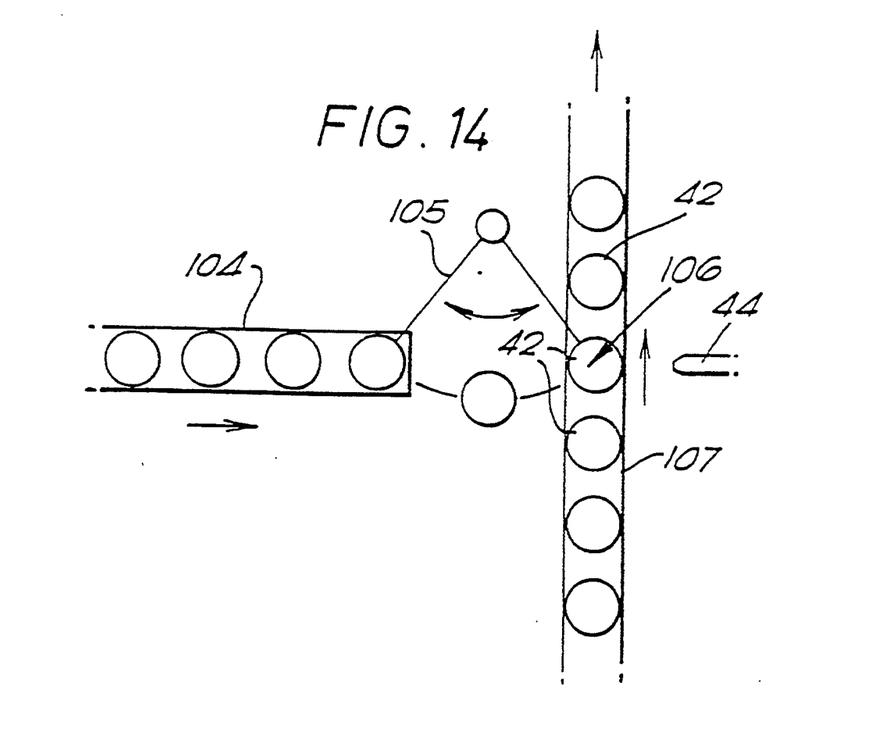
FIG. 14 is a diagrammatic plan view an embodiment of the invention for operating on plantlets during micropropagation.

The main modification of the embodiments shown in FIGS. 13a and b and 14, is that each container of plantlets is operated on in accordance with the invention when inverted with the plants facing downwardly relative to their normal growing positions. FIG. 13a shows an inverted container 42 of plantlets 43 having an attached lid. As shown in FIG. 14, the container 42 is brought by an overhead conveying means 104 and transfer arm 105 to a work station 106. At this position the normally upper position 36 (shown in FIG. 13a as being inverted and therefore in a lower position than the nutrient material 45) is cut by the laser 44 at a line Y in FIG. 13a. The cut is positioned within the part of the container filled by the nutrient medium 45 that is to say at a level which, if the container where in its normal position, would be below the level of the nutrient material.

As shown in FIG. 13b, a new container 42 is positioned in its normal orientation on a conveyor belt 107 immediately below the inverted container 42 at the work station 106. As the portion 36 to be removed is cut by the laser 44 an air jet is applied, as has been described previously, to blow the cut portion of container away from the conveyor belt 107. After this portion has been removed, the laser 44 is then utilised to cut a series of lines through the inverted plantlets, in a similar manner as shown in at A to I in FIG. 11 but in the reverse order to that described with reference to FIG. 10. This is achieved by the following steps. Firstly the inverted container 42 is raised (by means not shown) until the cut line L in FIG. 13b is level with the horizontal position of the laser 44. The laser 44 is then traversed across the inverted plantlet at the cut line L, allowing cut portions of plant to fall into the fresh container 42 of nutrient medium 45 which has been carried to the work station by the conveyor belt 107. The next step is that the conveyor belt 107 moves another fresh container 42 to the work station 104 beneath the inverted container 42, and the inverted container 42 is lowered relative to the laser 44 until the next cutting line M is level with the horizontal plane of the laser. The laser 44 is then traversed by the apparatus previously described with reference to FIG. 12, across the cut line M in FIG. 13b and a further series of plant portions is dropped onto the new nutrient medium in the new container 42. This continues until all the required cuts of the plantlets have been completed. The inverted container 42 with the remaining root portions of the plantlets is then removed by the support arm 105 to a disposal area, not shown, and is released into the disposal area. A further inverted container 42 is then grasped by the support arm 105 from the input conveyor 104 and is brought to the main work station opposite laser at 44. The procedure is then repeated.

It is a particular advantage of the embodiment which has been described with reference to FIGS. 13a and b and 14, that there is no component which must come in contact with the container and the plants. Consequently the system has no requirement for repeated tool sterilisation.

It is to be appreciated that where reference is made to the advantages of cutting the container below the level of the nutrient medium in the container, it is meant that the cut must be below the normal level of the container when the container is in the normal upright growing position. When the container is inverted for cutting, the cutting level is of course above the level of the nutrient medium in the container.

It is also to be appreciated that at least some of the advantages of the embodiment of FIGS. 13 and 14 can be obtained by having the container inclined to the vertical, rather than horizontal and completely inverted. For example, the method may be combined with use of an air blast to remove cut pieces of plant, if the container is held vertical with the plants extending horizontally during cutting.

We claim:

1. A method of operating on plantlets during micropropagation comprising the steps of:
   presenting at a work station a closed, sterilized container containing plantlets growing in a nutrient medium;
   cutting open the container by a laser to provide access to the plantlets; and
   then performing an operation on the plantlets in the opened container.

2. A method according to claim 1 in which the container has a first portion extending in the region of the nutrient medium and a second portion extending in the region in which the plantlets grow, the method including;
   using the laser to cut the second portion of the container free from the first portion which contains the nutrient medium supporting the plantlets; and
   removing the second portion of the container to provide access to the plantlets.

3. A method according to claim 2 in which said container is cut in such a manner that, when cut, the second portion falls apart free from the first portion.

4. A method according to claim 1 including cutting a side wall or side walls of a container by the laser.

5. A method according to claim 4 including the step of cutting the container by the laser at a level within the depth of nutrient medium in the container.

6. A method according to claim 4 including the step of focusing the beam of the laser to a cutting focus at a side wall of the container, and rotating the container during the cutting of the container.

7. A method according to claim 1 in which said operation on the plantlets in the opened container comprises removing by robotic handling means a plantlet from the container.

8. A method of operating on plantlets during micropropagation including the steps of:
   growing plantlets in a container containing the plantlets growing in a nutrient medium, the container having a first portion extending in the region of the nutrient medium and a second portion extending in the region in which the plantlets grow, the container being positioned in a first orientation while the plantlets are growing with the second portion at a higher level than the first portion;
   presenting the container at a work station in a second orientation, different from the first orientation, with the second portion of the container at a lower level, relative to the first portion, than is the case in the first orientation; and
   cutting the container by a laser to provide access to the plantlets.

9. A method according to claim 8 in which the container is presented at the work station in an inverted position with the plantlets extending downwardly from the nutrient medium.

10. A method according to claim 8 including removing the cut away upper portion at least partly by gravity.

11. A method of operating on plantlets during micropropagation including the steps of:
    growing plantlets in a container containing the plantlets growing in a nutrient medium, the container being positioned in a first orientation while the plantlets are growing, the plantlets having base portions adjacent the nutrient medium and distal portions growing upwardly away from the nutrient medium;
    cutting the container by a laser to provide access to the plantlets;
    presenting the plantlets at a work station in a second orientation different from the first orientation, with the distal portions of the plantlets at a lower position relative to the base portions than is the case in the first orientation;
    cutting by the laser through a plurality of the growing plantlets to release in bulk cut-away portions large enough to contain tips and/or nodes.

12. A method according to claim 11 in which the plantlets are presented for cutting with the container inverted and the plantlets extending downwardly from the nutrient medium.

13. A method according to claim 2 including removing the cut away plant portions from the remaining plantlets at least partly by gravity.

14. A method according to claim 2, including the step of receiving the released plant portions onto a second nutrient medium positioned below the plantlets in the first container.

15. A method of operating on plantlets during micropropagation comprising the steps of:
    presenting at a work station a closed, sterilized container containing plantlets growing in a nutrient medium;
    cutting open the container by a laser to provide access to the plantlets; and
    using the laser also to cut a portion of plant tissue from at least one of said plantlets.

* * * * *

UNITED STATES PATENT AND TRADEMARK OFFICE
CERTIFICATE OF CORRECTION

PATENT NO.    :    5,382,268
DATED         :    JANUARY 17, 1995
INVENTOR(S)   :    BROWN et al

It is certified that error appears in the above-identified patent and that said Letters Patent is hereby corrected as shown below:

On the title page, item [86]:

Please change:

"[86]  PCT No.:  PCT/GB90/01447

§ 317 Date:   March 2, 1992

§ 102(e) Date:   March 2, 1992 to

--[86]  PCT No.:  PCT/GB90/01447

§ 317 Date:  March 20, 1992

§ 102(e) Date :  March 20, 1992

Signed and Sealed this

Twelfth Day of September, 1995

Attest:

BRUCE LEHMAN

Attesting Officer    Commissioner of Patents and Trademarks